United States Patent
Signaevsky et al.

(10) Patent No.: US 10,845,667 B2
(45) Date of Patent: Nov. 24, 2020

(54) PHOTOSENSITIVE MULTILAYERED COMPOSITE MATERIAL SUITABLE FOR EYE IMPLANTS

(71) Applicant: NeuroSilica, Inc., Wilmington, DE (US)

(72) Inventors: Maxim Signaevsky, Brooklyn, NY (US); Igor Yehuda Yaroslavsky, Vancouver (CA)

(73) Assignee: NEUROSILICA, INC., Wilmington, DE (US)

( * ) Notice: Subject to any disclaimer, the term of this patent is extended or adjusted under 35 U.S.C. 154(b) by 0 days.

(21) Appl. No.: 16/426,676

(22) Filed: May 30, 2019

(65) Prior Publication Data

US 2019/0369454 A1    Dec. 5, 2019

Related U.S. Application Data

(60) Provisional application No. 62/678,004, filed on May 30, 2018.

(51) Int. Cl.
*G02F 1/1524*    (2019.01)
*G02B 27/14*    (2006.01)
(Continued)

(52) U.S. Cl.
CPC ....... *G02F 1/15245* (2019.01); *G02B 27/142* (2013.01); *G02B 27/4294* (2013.01);
(Continued)

(58) Field of Classification Search
CPC .... G02B 27/14; G02B 27/42; G02B 27/4294; G02B 27/142; G02B 5/206; G02B 5/223;
(Continued)

(56) References Cited

U.S. PATENT DOCUMENTS 3,864,163 A    2/1975    Beer
4,857,094 A    8/1989    Groth et al.
(Continued)

FOREIGN PATENT DOCUMENTS

WO    2008/047144 A1    8/2008

OTHER PUBLICATIONS

Bartosewicz, B. et al., "Synthesis and characterization of noble metal—titania core—shell nanostructures with tunable shell thickness" Beilstein J. Nanotechnol (Oct. 2017) pp. 2083-2093, vol. 8.
(Continued)

*Primary Examiner* — Jie Lei
(74) *Attorney, Agent, or Firm* — Tutunjian & Bitetto, P.C.

(57) ABSTRACT

A multilayered structure that includes a light receiving section including at least one layer including a noble metal composition and a metal oxide composition, the light transducing section transducing the energy of photons received to the energy of electrons. The structure further includes a piezo composite amplifier layer comprising a piezo polymer matrix, a first dispersed phase of piezo nanoparticles and a second dispersed phase of carbon nanotubes. The piezo composite amplifier amplifying a signal from the energy of the electrons received from the light receiving section using piezo-electric effects. The nanostructure further includes an environmental interface layer for delivering the amplified signal received from the piezo composite amplifier layer to a biological environment.

15 Claims, 5 Drawing Sheets

(51) Int. Cl.
  G02B 27/42 (2006.01)
  G02F 1/1333 (2006.01)
(52) U.S. Cl.
  CPC ............ *G02F 2001/133394* (2013.01); *G02F 2201/086* (2013.01); *G02F 2202/022* (2013.01); *G02F 2202/14* (2013.01); *G02F 2202/36* (2013.01)

(58) Field of Classification Search
  CPC ............... G02F 1/1524; G02F 1/15245; G02F 2001/133394; G02F 2001/086; G02F 2202/022; G02F 2202/14; G02F 2202/36; A61N 1/0543; A61N 1/36046; A61B 5/04001; B82Y 20/00
  USPC ........ 359/273, 245, 315, 322, 484; 977/953, 977/954, 742, 762, 894, 837, 868
  See application file for complete search history.

(56) References Cited

U.S. PATENT DOCUMENTS

| | | |
|---|---|---|
| 9,738,788 B1 | 8/2017 | Gross et al. |
| 2008/0288067 A1 | 11/2008 | Flood |
| 2009/0146140 A1 | 6/2009 | Kim et al. |
| 2009/0302714 A1 | 12/2009 | Kim |
| 2012/0065704 A1 | 5/2012 | Kavasssery et al. |
| 2017/0228072 A1 | 8/2017 | Amin et al. |
| 2018/0214042 A1 | 8/2018 | Signaevsky et al. |

OTHER PUBLICATIONS

Im, M. et al., "Temporal properties of network-mediated responses to repetitive stimuli are dependent upon retinal ganglion cell type" Journal of Neural Eng. (Feb. 2016) pp. 1-13, vol. 12, No. 2.

Hwang, B. et al., "Highly Flexible and Transparent Ag Nanowire Electrode Encapsulated with Ultra-Thin Al2O3: Thermal, Ambient, and Mechanical Stabilities" Scientific Reports (Jan. 2017) pp. 1-7, vol. 7, Article No. 41336.

Kohler, J.M. et al., "Single-Photon-Single-Electron Transition for Interpretation of Optical Spectra of Nonspherical Metal Nanoparticles in Aqueous Colloidal Solutions" Journal of Nanomaterials (Aug. 2018) pp. 1-8, vol. 2018, Article ID 1781389.

Sun, Y. et. al., "Non-symmetric hybrids of noble metal-semiconductor: Interplay of nanoparticles and nanostructures in formation dynamics and plasmonic applications" Progress in Natural Science: Materials International (Apr. 2017) pp. 157-168, vol. 27, Issue 2.

Bae, S. et al., "Roll-to-roll production of 30-inch graphene films for transparent electrodes" Nat. Nanotech. (Jun. 2010) pp. 574-578, vol. 5.

Saigal, R. et al., "Electrical Stimulation via a Biocompatible Conductive Polymer Directs Retinal Progenitor Cell Differentiation" Conf Proc IEEE Eng Med Biol Soc. (Jun. 2013) pp. 1627-1631, vol. 2013.

Haggren, T. et al., "Nanowire encapsulation with polymer for electrical isolation and enhanced optical properties" Nano Research (Aug. 2017) pp. 2657-2666, vol. 10, Issue 8.

Bowmaker, J.K. et al., "Visual pigments of rods and cones in a human retina" J Physiol. (Jan. 1980) pp. 501-511, vol. 298.

Fuchs, P. et al., "Low-pressure plasma cleaning of Au and Pt noble metal surfaces" Applied Surface Science (Dec. 2009) pp. 1382-1390, vol. 256, Issue 5.

Verkhovtsev, A.V. et al., "Revealing the Mechanism of the Low-Energy Electron Yield Enhancement from Sensitizing Nanoparticles" Physical Review Letters (Feb. 2015) pp. 063401-1-063401-6.

PHOTOSENSITIVE MULTILAYERED COMPOSITE MATERIAL SUITABLE FOR EYE IMPLANTS

CROSS REFERENCE TO RELATED APPLICATIONS

This application claims the benefit of U.S. Provisional Application No. 62/678,004 filed May 30, 2018, titled "A novel photosensitive multilayered composite material suitable for eye implants", which is incorporated herein in its entirety by reference.

BACKGROUND

Technical Field

The present invention generally relates to composite materials applied to biological environments, and more particularly to composite materials for photon-electron transduction.

Description of the Related Art

Effort has been devoted to the development of microelectronic retinal prosthetics with the goal of restoring sight to the blind. Electrically elicited vision can be useful for performing tasks of daily living in those blinded. Continuous effort is widely being made to provide a functional photosensitive retinal prosthetics with the pixilated signal transduction to the visual pathway of the brain. Unfortunately, however, none these attempts brought satisfactory results to date.

SUMMARY

The methods and structures described herein can provide a composite material technology for photon-electron transduction based on broadband photo-absorption. The proposed composite will be able to receive photons on one end, transduces their energy into the energy of electrons, amplify the signal using direct and reverse piezo-electric effects, and deliver the resulting electrical impulses onto nervous tissue, brain or optic nerves. Multiple embodiments assembled together will be able to transduce a pixilated image to the visual pathway of the brain, and, therefore, the disclosed methods and structures can function as an "artificial retina+ optic nerve" complex.

In accordance with an embodiment of the present disclosure, a multilayered microstructure comprising layers of functional nano-composited is provided that includes a light receiving section including at least one layer including at least one of a noble metal alloy composition and a metal oxide (e.g. $TiO_2$) composition. The light receiving section transduces the energy of photons received by the light receiving section to an energy of electrons. The microstructure further includes a piezo composite amplifier layer that includes a piezo polymer matrix, a first dispersed phase of piezo nanoparticles and a second dispersed phase of carbon nanotubes. The piezo composite amplifier amplifying a signal from the energy of the electrons received from the light receiving section using piezo-electric effects. The microstructure further includes an environmental interface layer for delivering the amplified signal received from the piezo composite amplifier layer to a biological environment. For pixilation, the structures described herein may use technology similar to semiconductor production technology, such as technology directed to charge-coupled device (CCD) cameras.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
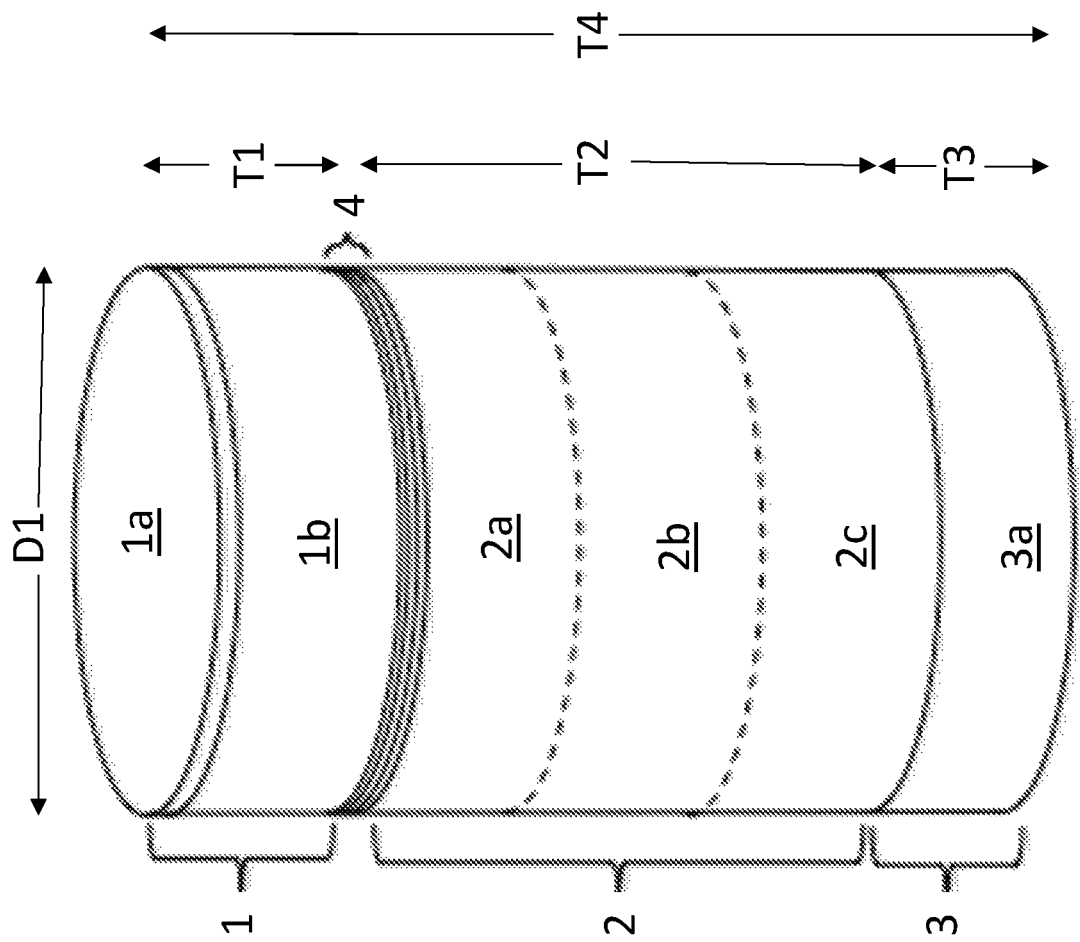
FIG. 1 is a perspective view of a stacked unit of layers of a composition, in which the stacked unit is able to receive photons on one end, transduces their energy in to the energy of electrons, amplify the signal using direct and reverse piezo-electric effects, and deliver the resulting electrical impulses onto nervous tissue, brain or optic nerves, in accordance with one embodiment of the present disclosure.

Detailed embodiments of the claimed structures and materials are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment. For purposes of the description hereinafter, the terms "upper", "over", "overlying", "lower", "under", "underlying", "right", "left", "vertical", "horizontal", "top", "bottom", and derivatives thereof shall relate to the embodiments of the disclosure, as it is oriented in the drawing figures. The term "positioned on" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, or insulating layers at the interface of the two elements.

The methods and structures described herein provide a composite material technology for photon-electron transduction based on broadband photo-absorption. The basis of the methods and structures that are described herein is the photosensitive multilayered composite material that transduces photon energy in the visible light spectrum (wavelengths from about 390 to 700 nm), and partially ultraviolet for selected purposes, into electron energy. In some examples, the stacked structure 100 provided herein can receive a photon, convert it to an electron and transport the electron to a neuron, in a manner suitable for use in prosthetic devices. In some embodiments, the structures and corresponding methods employing the structures described herein can reduce radio-hazard risk by employing a no-ionization radiation method.

In some embodiments, the methods and structures employ core-shell nanostructures (CSNs) in combination with electron excitation in metals and multilayered composite amplifying layers to provide photosensitive materials suitable for biological environments, such as materials that can be used in eye implants.

FIG. 1 is a perspective view of a stacked unit 100 of layers of different compositions, in which the stacked unit 100 is able to receive photons on one end, transduces their energy in to the energy of electrons, amplify the signal using direct and reverse piezo-electric effects, and deliver the resulting electrical impulses onto visual pathway nervous tissue, brain and/or optic nerves, in accordance with one embodiment of the present disclosure. In some embodiments, assembled units 100 in a brush-like structure or a bundle of cables for receiving photons, and thereafter converting the energy from the photons to electrical impulses. In some embodiments, the proposed technology functions as an "artificial retina+ optic nerve" complex, and therefore can be suitable for eye implants.

In one example, the stacked structure 100 may include a first section 1 that is composed of a first layer 1a of titanium dioxide ($TiO_2$), and a second layer 1b composed of core shell nanoparticles of noble metal nanoparticles, e.g., gold (Au), iridium (Ir), platinum (Pt) or their alloys, covered in a shell of metal oxide material, e.g., $TiO_2$, embedded in a dielectric polymer together with vertically polarized carbon nanotubes (CNT), or a solid noble metal layer (Au, Ir, Pt or their alloys). The second section 2 of the stacked structure 100 provides a piezo-composite amplifier composed of at least three sublayers. For example, the second section 2 may include a first layer 2a having a composition including piezo-polymer at approximately 20 wt. %, piezo-ceramics at approximately 80 wt. %, and carbon nanotubes (CNT) at approximately 0.2 et. %; a second layer 2b having a composition of piezo-polymer at approximately 30 wt., piezo-ceramics %, at approximately 70 wt. %, and carbon nanotubes (CNT) at approximately 0.3 wt. %; and a third layer 2c having a composition of piezo-polymer at approximately 20 wt. %, piezo-ceramics at approximately 80 wt. %, and carbon nanotubes (CNT) at approximately 0.2 wt. %. At least one interface layer may be present between the first and second sections 1, 2 of the stacked structure, which can be composed of graphene. The stacked structure 100 may also include a third section 3. The third section 3 may provide a biological environment interface layer 3a which may be exemplified as noble metal nanoparticles embedded in the dielectric polymer, a noble metal alloy grid, nanowires (e.g., silver (Ag) nanowires) or a combination thereof. It is noted that this example is not intended to be limiting, as other compositions for each of the components are further contemplated. Further details of the stacked structure are now provided in greater detail with reference to FIGS. 1-5.

Referring to FIG. 1, the stacked structure 100 that is a basic unit may include three main sections with sublayers present therein. The structure depicted in FIG. 1 is an illustration of basic unit of the stacked structure 100 that can be suitable for biological applications, such optical applications. The stacked structure 100 depicted in FIG. 1 is in the geometry of a rod. When employing a plurality of these rods, a brush geometry (also referred to as form factor) is provided. The brush can be used as a photosensitive and transducing part of an eye implant. The stacked structure 100 is a microstructure having an overall height, i.e., thickness T1, that can range from 150 nm to 200 nm. In one example, the height, i.e., thickness T1, of the stacked structure 100 is equal to approximately 100 nm. In some embodiments, the diameter D1 of the stacked structure 100 may range from 30 nm to 50 nm. In one example, the diameter D1 of the stacked structure may be equal to 40 nm. It is noted that these dimensions are provided for illustrative purposes and are not intended to limit the present disclosure, as other dimensions are equally applicable.

The first section identified by reference number 1 may be the light receiving end of the stacked structure 100. The first section 1 may absorb photons of light and transduces their energy into electron energy.

In some embodiments, the first section identified by reference number 1 includes a metal oxide layer 1a and a noble metal containing layer 1b. The second section of the stacked structure 100 that may be employed in eye implants for restoring vision, which is identified by reference number 2, may include three sublayers 2a, 2b, 2c, and may provide piezo-composite amplifier layer. The third section 3 of the stacked structure 100 can provide an environmental interface layer 3, in which the interface layer 3 may be composed of noble metal nanoparticles in a dielectric polymer matrix or a layer of metal nanowires.

In some embodiments, the first layer 1a of the first section 1 may be composed of a metal oxide, such as titanium oxide ($TiO_2$) or titanium oxide ($TiO_2$) with a modification of anatase with tin oxide (SnO). The first layer 1a of the first section 1 may include titanium dioxide ($TiO_2$) that is modified with titanium dioxide ($TiO_2$) with modification of antase with SnO [Sn(II)] nanoclusters supported to design photocatalysis with increased intension absorption and significant reduction of charger carrier recombination. It is noted that titanium oxide is only one example of a composition that is suitable for the first layer 1a of the first section 1. For example, in some embodiments, the first layer 1a of the first section 1 may be tantalum oxide, tungsten oxide, or other like metal oxides.

The second layer 1b of the first section 1 of the stacked structure 100 may include a noble metal based layer that absorbs photons and transduces their energy into electron energy. There are two prominent mechanisms of electron excitation in metals. Plasmons, i.e. collective excitations of delocalized valence electrons, dominate the spectra of electron emission from metallic nanoparticles in the energy range of about 1 eV-10 eV. The main contribution to the electron yield arises from the atomic giant resonance associated with the collective excitation of 5 d electrons in individual atoms of a nanoparticle. Similar to the photoionization, the two distinct types of collective electron excitations appear in the process of impact ionization. Therefore, noble metal nanoparticles, especially those made of gold and platinum, significantly enhance electron yields due to the collective response to an external electric field.

In most examples, noble metals have no band gap and possess a high density of free electrons. In some embodiments, such physical and electrical properties provide photovoltaic effect with high electrical and thermal conductivity as well as a wide range of absorption and effective reflection of light. In plasmons the electron yield arises from the atomic giant resonance associated with collective excitation of 5 d electrons of a noble metal nanoparticle.

In some embodiments, the noble metal-based layer, e.g., second layer 1b of the first section 1, absorbs photons and transduces their energy into electron energy. The noble metals for the second layer 1b that are suitable for the second layer 1b are metals that are resistant to corrosion and oxidation in moist air. In one embodiment, a list of chemically noble metals that are suitable for the second layer 1b include ruthenium, rhodium, palladium, silver, osmium, iridium, platinum, gold and combinations thereof. In one another embodiment, a list of chemically noble metals that are suitable for the second layer 1b include one or more of mercury, rhenium and copper as noble metals.

It has been determined, that the surface plasmon resonance properties of noble metals, such as gold and silver nanoparticles (NPs), can increase the optical absorption of metal oxides, such as $TiO_2$, and extend its absorption band to the visible light region. As such, core shell nanostructures (CSNs) can overcome one of the most important limitations in broader use of $TiO_2$, i.e., the spectrum limitation for UV light ($\lambda<400$ nm).

Figure 2:
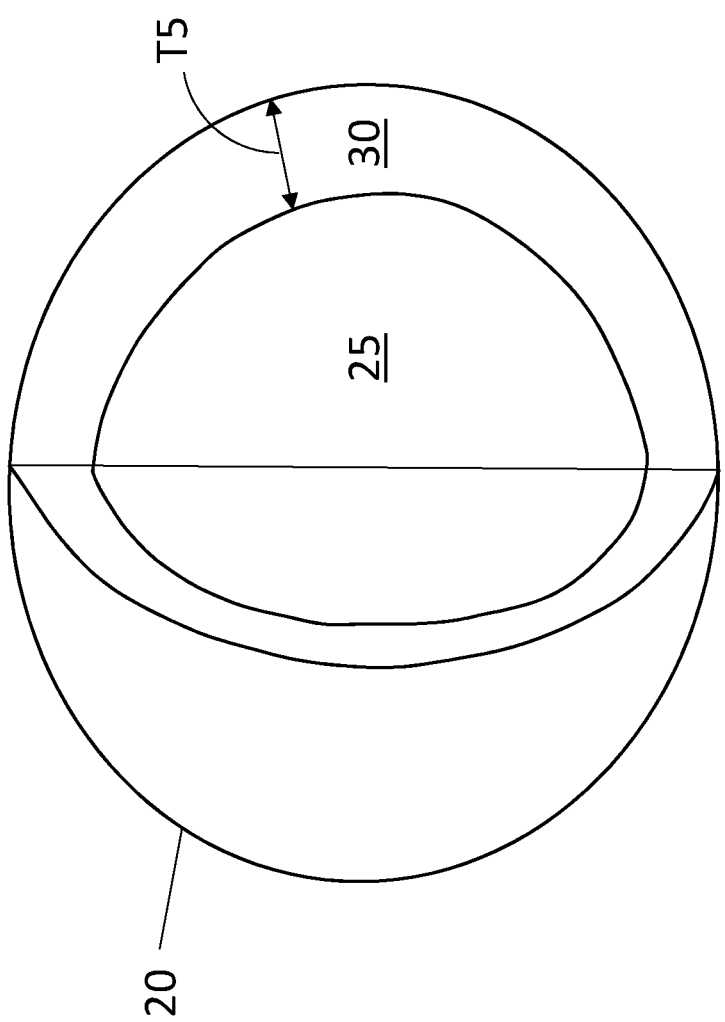
FIG. 2 is a sectioned perspective view of a core shell nanoparticles of noble metal nanoparticles covered in a shell of metal oxide material, in accordance with one embodiment of the present disclosure.

In some embodiments, to enhance photovoltaic properties the second layer 1b of the second section 1 includes core-shell nanostructures (CSN) 20 with noble metal (e.g. Au, and/or Ag) nanoparticles (NPs) as a core 25 and metal oxide shell, such as $TiO_2$ as a shell material 30. FIG. 2 is a sectioned perspective view of a core shell nanoparticles (CSNs) 20 of noble metal nanoparticles 25 covered in a shell 30 of metal oxide material. In some embodiments, the core-shell nanostructures (CSN) 20 include a gold core 25 with a titanium oxide shell (Au@$TiO_2$) 30, or a silver core 25 with a titanium oxide shell (Ag@$TiO_2$) 30.

The combination of the shell 30 of metal oxide, such as a $TiO_2$ metal shell, and the core 30 noble metal nanoparticles in a form of core-shell nanostructures (CSNs) 20 enhances optical absorption across the spectrum of visible light, as well as an ultraviolet spectrum ($\lambda<400$ nm).

In some embodiments, the noble metal-based layer that provides the second layer 1b of the first section 1 for the stacked structure 100 may be composed of noble metal nanoparticles coated with a metal oxide composition that are embedded in dielectric polymer with polarized carbon nanotubes (CNTs). The term "nanoparticle" denotes a particle having a maximum diameter that is less than 100 nm. In some embodiments, the noble metal layer is composed of nanoparticles of Au, Ir, Pt, and Ag and/or their alloys covered by $TiO_2$ to form core-shell nanostructures (CSN) 20 with tunable shell thickness T5, e.g., metal oxide thickness. In one embodiment, the metal oxide shell 30, e.g., titanium oxide ($TiO_2$) shell, has a thickness T5 ranging from 40 nm to 70 nm for a nanoparticle core 25 of gold (Au). In one embodiment, the metal oxide shell 30, e.g., titanium oxide ($TiO_2$) shell, has a thickness T5 ranging from 45 nm to 95 nm for a nanoparticle core 25 of gold (Au) (Au@ $TiO_2$).

In some embodiments, the nanoparticles 20 may be provided by a core 25 of noble metal composition, such as gold (Au), iridium (Ir), platinum (Pt) or alloys thereof, that is covered in a metal oxide coating 25, such as titanium dioxide ($TiO_2$) coating, and embedded in a dielectric polymer with vertically polarized carbon nanotubes (CNT). The word "polymer" can be defined as a material made of a large number of repeating units, which are linked to each other through chemical bonding. A single polymer molecule may contain millions of small molecules or repeating units which are called monomers. Polymers are very large molecules having high molecular weights. "Nanotube" as used herein is meant to denote one form of nanostructure having an aspect ratio of length to width greater than 10. The term "nanotube" includes single wall and multi-wall nanotubes unless specifically specified as distinct. In one embodiment, a carbon nanotube is at least one graphene layer wrapped into a cylinder or a truncated cone. In one embodiment, a single wall carbon nanotube is a graphene rolled up into a seamless cylinder with diameter of the order of a nanometer. A multi-wall carbon nanotube is a plurality of graphene sheets rolled up into a seamless cylinder with diameter of the order of a nanometer.

In this example, the dielectric polymer can be considered a matrix material, and the metal oxide coated nanoparticles of noble metals can be a dispersed phase within the matrix material. The dielectric polymer can be optically transparent. For example, the dielectric polymer may be provided by a polycarbonate containing composition.

In another embodiment, the second layer 1b of the first section 1 of the stacked structure 100 can be a solid noble metal layer. For example, the second layer 1b of the first section 1 may be composed of a solid metal layer, e.g., not including carbon nanotubes or other dispersed phases of composite like material, of gold (Au), iridium (Ir), platinum (Pt) or their alloys.

In yet another embodiment, the second layer 1b of the first section 1 of the stacked structure 100 is a solid noble metal layer, e.g., composed of gold (Au), iridium (Ir), platinum (Pt) or their alloys, that can/may be treated with plasma. The six platinum-group metals are ruthenium, rhodium, palladium, osmium, iridium, and platinum, which have similar physical and chemical properties. In the embodiments in which a noble metal layer can/may be treated with a plasma to enhance surface properties, the solid metal layer of noble metal may be composed of alloys of gold, silver, iridium, and platinum, rhodium in various combinations, which corresponds to the absorption of the various sectors of light. The layer of noble metal alloys has various absorption rate depending on the composition. Using low-pressure plasma selective etching, a pixilated surface can be provided with various alloy combinations per pixel, where every given pixel can correspond to the desired wavelength. For instance, the increase % of gold (Au) in a pixel alloy can provide a more intensive absorption of green light spectrum, whether the increase of % of platinum (Pt) in a pixel would correspond to the increased adsorption of yellow light.

In some embodiments, the thickness T1 of the first second 1 may range from 40 nm to 200 nm. In one example, the thickness of the first section 1 may be equal to 100 nm. It is noted that in addition to the above description of core shell nanoparticles, further details of additional embodiments of these structures can be found in the publication Huang wang et. al, "Exploiting Core-Shell Synergy for Nanosynthesis and Mechanistic Investigation", Accounts of Chemical research, 46(7), April 2013.

Referring to FIG. 1, an interface section 4 is present between the first section 1 and the second section 2 of the stacked structure 100. In one embodiment, the interface section 4 may include at least one highly conductive graphene layer. In some embodiments, graphene is a one atom thick layer of bonded carbon atoms arranged in a hexagonal or honeycomb lattice from which graphite may be composed. Although the interface section 4 that is depicted in FIG. 1 includes three layer of material, the present disclosure is not limited to only this example. For example, the interface section 4 may include different numbers of layers, such as a single material layer, two material layers, three material layers, four material layers, five material layers etc.

In some embodiments, the interface section 4 includes a highly conductive graphene layer that creates a gradient for electrons passing them as they travel from the core shell nanoparticle's (CSN's) photovoltaic layer of the second layer 1b of the first section 1 of the stacked structure 100 to the multilayer piezo-composite amplifier in the second section of the stacked structure 100. In one example, the graphene layer of the interface section 4 has a smooth surface topology that can prevent roughness-induced electrical shorts or degradation, providing high conductivity, light transparency with low electric impedance and a high degree of mechanical flexibility. These material of the interface section 4 between the first section 1 and the second section 2 of the stacked structure 100 are applicable for bio-medical applications.

In some other embodiments, the interface section 4 that is present between the first and second 1, 2 sections of the stack structure 100 are composed of a two-dimensional (2D) hybrid organic-inorganic perovskite film. In some embodiments, elucidating electron-phonon coupling in hybrid organic-inorganic perovskites provides an increasing high photovoltaic efficiency at the graphene level. A perovskite is any material with the same type of crystal structure as calcium titanium oxide ($CaTiO_3$), known as the perovskite structure, or $^{XII}A^{2+VI}B^{4+}X^{2-}_3$ with the oxygen in the edge centers. In some embodiments, the hybrid organic-inorganic perovskite film that can provide the interface section 4 may be selected from the group consisting of Methylammonium lead iodide ($MAPbI_3$), $CH_3NH_3PbI_3$, $HC(NH_2)_2PbI_3$, $CH_3NH_3SnI_3$, and combinations thereof.

The improved photovoltaic efficiency of the hybrid organic-inorganic perovskites can be attributed to polaronic effects involving stabilization of localized charge character by structural deformations and polarizations. Methylammonium lead iodide ($MAPbI_3$) perovskite exhibits excited-state coherent nuclear wave packets oscillating at ~20, ~43, and ~75 $cm^{-1}$ which involve skeletal bending, in-plane bending, and c-axis stretching of the I—Pb—I bonds, respectively. The amplitudes of these wave packet motions provide on the magnitude of the excited-state structural changes, in particular, the formation of a bent and elongated octahedral PbI64- geometry, the polaron formation via nuclear dynamics in perovskite structures, which can contribute to efficient charge separation and collection.

In yet another embodiment, the interface section 4 between the first section 1 and the second section 2 of the stacked structure 100 may include a combination of graphene layers and two-dimensional (2D) hybrid organic-inorganic perovskite films.

Referring to FIG. 1, the second section 2 of the stacked structure 100 is a multilayered piezo-composite amplifier layer.

Figure 3:
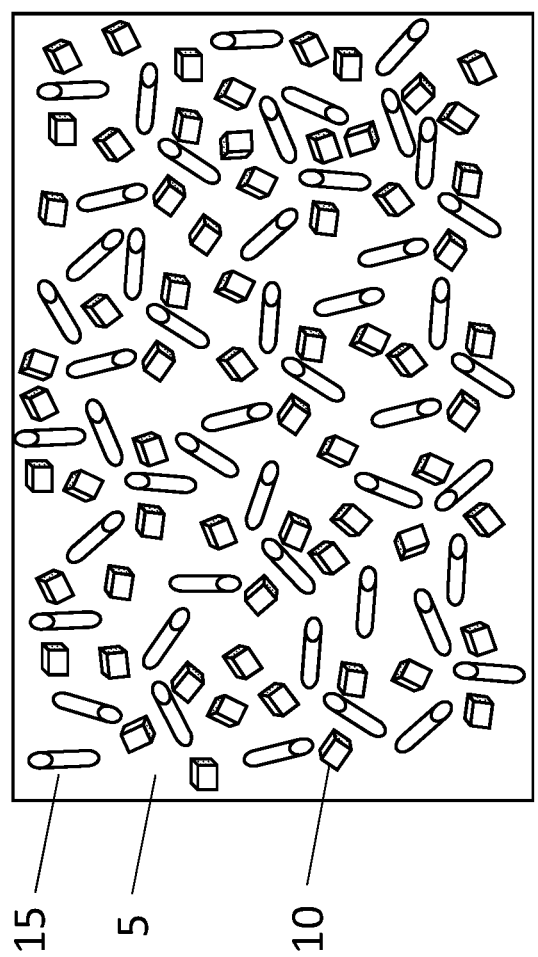
FIG. 3 is a cross sectional view of a layer composed of core shell nanoparticles of noble metal nanoparticles covered in a shell of metal oxide material embedded in a dielectric polymer together with vertically polarized carbon nanotubes (CNT), in accordance with one embodiment of the present disclosure.

Referring to FIG. 3 the piezo-composite amplifier layer is a composite of a piezo polymer 5, a piezo nanocrystal 10 and carbon nanotubes 15.

Referring to FIG. 3, a piezoelectric polymer 5 is a material having piezoelectricity, i.e., the ability of material, which is the property that the polarization of a material change by applying stress and/or strain generated by changing polarization). The piezoelectric polymer 5 provides the matrix of a composite structure. A composite is a material composed of two or more distinct phases, e.g., matrix phase and dispersed phase, and having bulk properties different from those of any of the constituents by themselves. As used herein, the term "matrix phase" denotes the phase of the composite that is present in a majority of the composite, and contains the dispersed phase, and shares a load with it. In the present case, the matrix phase may be provided by a polymer.

The word "polymer" can be defined as a material made from a large number of repeating units, which are linked to each other through chemical bonding. A single polymer molecule may contain millions of small molecules or repeating units which are called monomers. Polymers are very large molecules having high molecular weights. Monomers should have a double bond or at least two functional groups in order to be arranged as a polymer. This double bond or two functional groups help the monomer to attach two more monomers, and these attached monomers also have functional groups to attract more monomers. A polymer is made in this way and this process is known as polymerization. The result of polymerization is a macromolecule or a polymer chain. These polymer chains can be arranged in different ways to make the molecular structure of a polymer. The arrangement can be amorphous or crystalline. The main difference between amorphous and crystalline polymers is their molecular arrangement. Amorphous polymers have no particular arrangement or a pattern whereas crystalline polymers are well arranged molecular structures. Further details on the piezoelectric polymer are provided below.

In some examples, the piezo polymer 5 that provides the matrix for the composite may be polyvinylidene fluoride trifluoroethylene (PVDF-TrFE), which is a copolymer of PVDF. Polyvinylidene fluoride trifluoroethylene (PVDF-TrFE) can crystallize into β-phase directly from melt. In some embodiments, β-phase is thermodynamically favored for piezo-effect. In other examples, the piezo polymer material may have a composition that is selected from the group consisting of polyvinylidene flouride (PVDF), polyvinylidene fluoride (PVDF) copolymer with triflourethylene (TrFE), polyvinylidene fluoride (PVDF) copolymer with tetrafluorethylene (TFE), polyvinylidene fluoride (PVDF) copolymer with tetrafluorethylene (TFE) and triflourethylene (TrFE), nylon 11, poly(vinylidenecyanide vinylacetate), and combinations thereof.

Piezoelectric electric amplification are not only provided by the piezoelectric polymer 5, but are also provided by piezo nanocrystals 10 that are present as one dispersed phase of the composite. Crystalline solids or crystals, e.g., the piezo nanocrystals 10, have ordered structures and symmetry. The atoms, molecules, or ions in crystals are arranged in a particular manner; thus, have a long range order. In crystalline solids, there is a regular, repeating pattern; thus, we can identify a repeating unit.

In some embodiments, the piezo nanocrystal 10 is provided by a ceramic composition. Ceramics exhibiting piezoelectric properties can belong to the group of ferroelectric materials. One family of ceramic nanocrystals exhibiting piezo-electric properties include lead zirconate titanate (PZT); in which the members of this family consist of mixed crystals of lead zirconate ($PbZrO_3$) and lead titanate ($PbTiO_3$). Piezo-ceramic components have a polycrystalline structure comprising numerous crystallites (domains) each of which consists of a plurality of elementary cells. The elementary cells of these ferroelectric ceramics exhibit the perovskite crystal structure, which can generally be described by the structural formula $A^{2+}B^{4+}O_3^2$. The piezo nanocrystals may also include niobium (Nb) based crystals.

Similar to the piezoelectric polymer 5, the piezo electric nanocrystals 10 generate an electrical charge when mechanically loaded with pressure or tension, which is referred to above as the piezo effect. The piezo nanocrystals 10 are of a nanoscale. "Nanoscale" denotes that the piezo nanocrystals have a cross-section width that is less than 100 nm. In some examples, the piezo nanocrystals have a cross-sectional width ranging from 20 nm to 100 nm.

The piezo nanocrystals 10 provide one dispersed phase of the composite, in which the matrix phase of the composite is provided by a piezo polymeric material 5. As used herein, the term "dispersed phase" denotes a second phase (or phases) that is embedded in the matrix phase of the composite. The dispersed phase may be present throughout an entirety of the material that provides the matrix.

The piezo polymer material 5 and piezo nanocrystal 10 provide amplification of the electrical signal received from the first section 1 of the stacked structure 100, in which the amplified electrical signal is transmitted to the third section 3 of the stacked structure 100. In some embodiments, the addition of the first dispersed phase of the piezoelectric nano-material 10 in the form of nano-wires or nano-crystals into the matrix phase of the piezo polymer material 5 provides piezoelectric composition that can generate a high output power with higher efficiency when compared with other piezoelectric nanostructures. For example, nanowires of $Pb(Mg_{1/3}Nb_{2/3})O_3$—$PbTiO_3$ (PMN-PT) is one composition of piezo nanocrystals 10 that can dispersed throughout a matrix of a piezo polymer material 5 that is β-phase polyvinylidene fluoride trifluoroethylene (PVDF-TrFE), wherein the piezoelectric coupling coefficient (d33) of PMN-PT nanowires is about 371 pm/V, which is over 13 times higher than that of $BaTiO_3$ nanoparticles and 90 times higher than that of $NaNbO_3$ nanowires, which are approximately 28 and 4 pm/V, respectively. It is noted that this example is intended to be illustrative only, and not intended to limit the present invention. Other compositions are equally suitable for the piezo polymer 5 and the piezo nanocrystals 10.

In some embodiments, the piezo nanocrystal 10 can be composed of a piezo ceramic material. For example, the piezo ceramic material that provides the piezo nanocrystal 10 may have a composition selected from the group consisting of lead zirconate ($PbZrO_3$), lead titanate ($PbTiO_3$), and combinations thereof.

In one example, the material composition of the piezo nanocrystal 10 is a single-crystal piezoelectric $(1-x)PbZn_{1/3}Nb_{2/3}O_3-xPbTiO_3$ (PZNT) (further PMN-PT), which has a piezo-electric coupling coefficient (d33) up to 2500 pm/V, which is higher than that of conventional piezo-ceramics. For example, the piezoelectric coupling coefficient (d33) of single-crystal bulk PMN-PT is about 30 times higher than that of $BaTiO_3$, which is approximately 85.3 pm/V, and almost 4 times higher than that of PZT bulk material.

In another example, the material of the piezo nanocrystal 10 is Li-doped (K, Na)$NbO_3$ as a ceramic piezoelectric crystalline component. In yet another example, which may be suitable for long-term biocompatibility, lead free materials may be preferred. For example, the piezo nanocrystal 10 can be $Ba(Ce_xTi_{1-x}O_3)$, which is a mixture of Cerium-Barium Titanate (C-BT) with $(0.94(Bi_{0.5}Na_{0.5}TiO_3)+0.06(BaTiO_3))$ as a solid solution.

The first dispersed phase of piezo nanocrystals 10 may have a nanowire-type geometry, and in some instances can have a substantially spherical geometry. In the instances, in which the piezo nanocrystals 10 have a nanowire-type geometry, the piezo nanocrystals 10 have a cross-sectional width ranging from 20 nm to 100 nm, and the length of the piezo nanocrystals 10 can range from 100 nm to 500 nm. The dimensions of the piezo nanocrystals 10 are provided for illustrative purposes only, and are not intended to limit the present disclosure to this example.

Still referring to FIG. 3, the piezo-composite amplifier layer also includes a second dispersed phase of nanotubes, i.e., carbon nanotubes 15. The carbon nanotubes 15 provide pathways for distribution of the electrical impulses to a surface of the composite impulse generating layer contacting the biological environment. The carbon nanotubes 15 further provide for the delivery of the byproducts of the free radical degradation from the biological environment to piezo materials (both piezo-nanocrystals and piezo-polymer). The directional flow of the ions and charges is facilitated by the directional orientation of the nanoparticles, which can be achieved by poling.

Carbon nanotubes (CNT) 15 are cylindrical structures made of carbon with unique mechanical and electronic properties. Carbon nanotubes (CNTs) 15 are rolled up sheets of hexagonally ordered carbon atoms, giving tubes with diameters on the order of a few nanometers and lengths typically in the micrometer range. They may be single-walled or multiwalled (SWCNTs and MWCNTs respectively), and can be electrically conducting or semiconducting depending upon the orientation of the carbon lattice with respect to the tube axis (known as chirality in this context). In some embodiments, the carbon nanotubes (CNTs) 15 are designed to haphazardly penetrate polymer matrix, i.e., piezo polymer material 5. The function of the carbon nanotubes (CNTs) 15 are to collect, conduct, and accept electrons and toxic free oxygen radicals in intercellular space $[O^{3-}+C+e=CO_2]$, including those generated as a result of electric impulses delivery The carbon nanotubes 15 provide pathways for distribution of the electrical impulses. "Nanotube" as used herein is meant to denote one form of nanostructure having an aspect ratio of length to width greater than 10. The term "nanotube" includes single wall and multi-wall nanotubes unless specifically specified as distinct. In one embodiment, a carbon nanotube is at least one graphene layer wrapped into a cylinder. In one embodiment, a single wall carbon nanotube is a graphene rolled up into a seamless cylinder with diameter of the order of a nanometer. A multi-wall carbon nanotube is a plurality of graphene sheets rolled up into a seamless cylinder with diameter of the order of a nanometer.

In one embodiment, the carbon nanotubes 15 may have a high purity on the order of about 95% to about 99% carbon. In an even further embodiment, the carbon nanotubes 15 have a high purity on the order of about 99% or greater. In one embodiment, the carbon nanotubes 15 may be provided by laser vaporization. In one embodiment, the single wall carbon nanotubes 15 are formed using laser vaporization in combination with a catalyst, such as a metal catalyst. In one embodiment, the catalyst is supported on a substrate, such as a graphite substrate, or the catalyst may be floating metal catalyst particles. In one embodiment, the metal catalyst may be composed of Fe, Ni, Co, Rh, Y or alloys and combinations thereof.

The carbon nanotubes 15 comprise a majority of carbon typically being of high purity. In other examples, the carbon nanotubes include a carbon content ranging from being greater than 50%, wherein a purification process is utilized to provide carbon nanotubes having of high purity, such as greater than 90% carbon. In one embodiment, the carbon nanotubes may be purified by a process that includes an acid treatment followed by an oxidation. In one embodiment, the acid treatment may include treatment and oxidation steps are provided by a dilute $HNO_3$ reflux/air oxidation procedure.

The diameter of a single wall carbon nanotube 15 may range from about 1 nanometer to about 400 nanometers. In another embodiment, the diameter of a single wall carbon nanotube 15 may range from about 1.2 nanometers to about 1.6 nanometers. In one embodiment, the nanotubes 15 used in accordance with the present invention have an aspect ratio of length to diameter on the order of approximately 200:1 or greater. For example, the length of the carbon nanotubes (CNTs) 15 may be as great as 1 mm.

In some embodiments, the piezo-composite amplifier layer in section 2 of the stacked structure may include the piezo polymeric material 5 in an amount ranging from 70 wt. % to 84.9 wt. %; piezo nanocrystals 10 in an amount ranging from 15 wt. % to 30 wt. %; and carbon nanotubes 15 in an amount ranging from 0.1 wt. % to 1 wt. %. In one example, the piezo polymeric material 5 is present in the piezo-composite amplifier layer in an amount equal to 79.5 wt. %; the piezo crystal 10 are present in the piezo-composite amplifier layer in an amount equal to 20 wt. % and the carbon nanotubes 15 are present in an amount that is equal to 0.5 wt. %.

In one example, the piezo-composite amplifier layer may have a piezo-electric coefficient d33 ranging from 30-350 pC/N, and a polarization ranging from 2500-10000 $mC/cm^2$.

In some embodiments, the piezo polymer material 5 and the piezo nanocrystal 10 of the piezo-composite amplifier layer accepts electrons (by-product of free radicals degradation from the biological environment) thus re-charging the piezo-composite elements.

In one embodiment, the second section 2 of the stacked structure 100 provides a piezo-composite amplifier composed of at least three sublayers. For example, the second section 2 may include a first layer 2a of a piezo-composite amplifier composition having a composition including piezo-polymer 5 ranging from approximately 15 wt. % to approximately 20 wt. %, piezo-ceramic 10 ranging from approximately 75 wt. % to 80 wt. %, and carbon nanotubes (CNT) ranging from approximately 0.1 wt. % to approximately 0.5 wt. %. In one example, the first layer 2a of the piezo-composite amplifier composition for the second section 2 may have piezo polymer present at approximately 20 wt. %, piezo-ceramics at approximately 80 wt. %, and carbon nanotubes (CNT) at approximately 0.2 et. %.

In some embodiments, the second layer 2b of the second section 2 of the stacked structure 100 may have a piezo-composite amplifier composition that includes a piezo polymer 5 in an amount ranging from approximately 25 wt. % to 35 wt. %, a piezo-ceramic 10 in an amount ranging from approximately 65 wt. % to 75 wt. %, and carbon nanotubes (CNTs) in an amount ranging from 0.2 wt. % to 0.6 wt. %. In one example, the second layer 2b of the second section 2 of the stacked structure 100 may have a piezo-composite amplifier composition that includes piezo-polymer 5 at approximately 30 wt., piezo-ceramics 10 at approximately 70 wt. %, and carbon nanotubes (CNT) 15 at approximately 0.3 wt. %.

The third layer 2c of the second section 2 of the stacked structure 100 may have a piezo-composite amplifier composition that includes a piezo polymer 5 in an amount ranging from approximately 25 wt. % to 35 wt. %, a piezo-ceramic 10 in an amount ranging from approximately 65 wt. % to 75 wt. %, and carbon nanotubes (CNTs) in an amount ranging from 0.2 wt. % to 0.6 wt. %. In one example, the third layer 2c of the second section 2 of the stacked structure 100 may have a piezo-composite amplifier composition including a piezo-polymer 5 at approximately 20 wt. %, a piezo-ceramic 10 at approximately 80 wt. %, and carbon nanotubes (CNT) 15 at approximately 0.2 wt. %. It is noted that the above examples of the piezo composite amplifier composition is provided for illustrative purposes only. Further details regarding the composites for some embodiments that are employed in the second section 2 of the stacked structure 100 are described in U.S. patent application Ser. No. 15/883,793 filed Jan. 30, 2018, which is incorporated herein by reference.

The thickness T2 of second section 2 is may range from about 5 nm to about 30 nm. In one example, the thickness T2 of the second section is 10 nm.

Referring to FIG. 1, the vertically stacked structure 100 may include a third section 3. The third section 3 includes an environmental interface layer 3a. The environmental interface layer 3a may be a biological environment interface layer, which can be exemplified as noble metal nanoparticles embedded in the dielectric polymer. In this example, the noble metal nanoparticles may be similar to the core-shell nanostructures (CSN) with noble metal (e.g. Au, and/or Ag) nanoparticles (NPs) as a core and metal oxide shell, such as $TiO_2$, as a shell material, which is employed in the second layer 1b of the second section 1 of the vertically stacked structure 100. The dielectric polymer may be a transparent polymer, such as the polymeric composition that is described above with reference to the second layer 1b of the second section 1 of the vertically stacked structure 100. In some embodiments, the core-shell nanostructures (CSN) include a gold core with a titanium oxide shell (Au@$TiO_2$) or a silver core with a titanium oxide shell (Ag@$TiO_2$).

In another embodiment, the third section 3 may be a noble metal alloy grid. The noble metals used in the noble metal alloy grid have been described above, which may include gold (Au), silver (Ag), platinum (Pt) or combinations thereof.

In some other embodiments, the environmental interface layer 3a is composed of nanowires, such as silver (Ag) nanowires. In some other embodiments, the environmental interface layer 3a is composed of a combination of nanowires, e.g., silver (Ag) nanowires, and noble metal nanoparticles in a dielectric polymer.

In each of the aforementioned examples of compositions for the environmental interface layer 3a of the third section 3, the material layers may be treated with plasma for enhanced pixilation. Some embodiments, of the plasma treatment for the environmental interface layer 3a of the third section 3 is similar to the plasma treatment applied to the second layer 1b of the first section 1 of the vertically stacked structure 100.

The thickness T3 of third section 3 may range from about 100 nm to about 150 nm. In one example, the thickness T3 of the third section is 120 nm.

In some embodiments, electrons of various energies exit the piezo-composite amplifier layer 2a, 2b, 2c of the second section 2 of the vertically stacked structure 100 onto a pixilation grid and/or biological interface layer of the third section 3 of the vertically stacked structure 100. In some embodiments, when the vertically stacked structures 100 are assembled into a brush/cable/array, the light receiving end for receiving photons may be provided by the first section of the stacked structure 100, and at the other side of the vertically stacked structure 100, a pixelated amplified signal is transmitted from the third section 3.

In some embodiments, the vertically stacked structure 100 may be integrated into a nanofiber containing cable.

In some embodiments, the pixelated amplified signal can be further transferred to an end face of the silver nano-fiber cable, and optic nerve/tract or onto visual system of the brain.

In some embodiments, leaving the cable, the signal further comes onto a layer described previously as "biological environment interface layer", from which the signal is further accepted by a multilayered piezo-composite. Piezo-composite options are described in U.S. patent application Ser. No. 15/883,793 in great details, which is incorporated herein. The signal is further directly accepted by neurons and neuronal network.

In another example, a brush/cable/array including the vertically stacked structure 100 (as depicted in FIG. 6) is attached to the stump of the optic nerve or the optic tract and is further accepted by the visual system.

Being arranged in a cable-like fashion, the vertically stacked structure 100 described with reference to FIG. 1 can achieve the theoretical resolution up to (pixels per cm$^2$) is 6.25E+10/cm$^2$ (62.5 billion pixels per square centimeter). The photons of light are coming onto an end face of a brush-like array comprised vertically oriented thin fiber-like (or rod-like) elements. Each element is insulated from others with cross-linked polyethylene or parylene-C. Such insulation functions as an efficient antireflection electrical isolation coating for the vertical rod-like structures, with reflectivity down to <1% in the visible spectrum, which enhances photoluminescence intensity with low electron conductivity.

In some embodiments, on the other end of the brush, a pixelated amplified signal is received, which is further transferred to the front end face of the silver nano-fiber cable, which may be a highly flexible and transparent silver (Ag) nanowire electrode encapsulated with ultra-thin $Al_2O_3$ having a radius as great as 30 nm.

Leaving the cable, the signal further comes onto a layer described previously as "biological interface layer", from which the signal is further accepted by a multilayered piezo-composite. Piezo-composite options are described in U.S. patent application Ser. No. 15/883,793 filed Jan. 30, 2018, which is incorporated herein by reference. The signal is further directly accepted by neurons and neuronal network.

Figure 4:
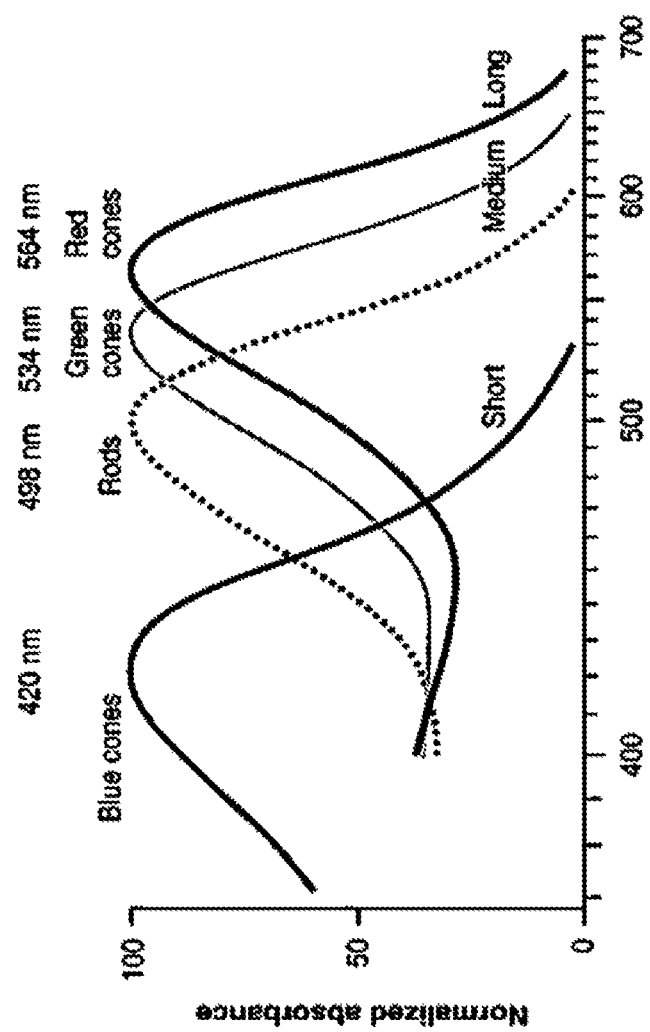
FIG. 4 is a plot of normalized absorption as a function of wavelength, in accordance with one embodiment of the present disclosure.

Referring to FIG. 1, it is noted that the basic design can be modified in such a way that some vertical stacked structures 100 will be tuned to be more sensitive to the range of the energy of the photons (intensity of the light, lumens); whereas other vertically stacked structures 100 will be tuned to the light of different wave lengths (colors). Combined, these two sub-types of vertically stacked structures 100 will mimic the retina of the human eye structure with rod cells being responsible for light brightness, and cones being responsible for color vision reacting to the light of various wavelength. FIG. 4 is a plot of normalized absorption as a function of wavelength including wavelengths visible to the human eye structure. On average the ratio rods to cons is approximately 20:1.

The shell core nanoparticles (SCNs) 10, e.g., the shell core nanoparticles (SCNs) within the second layer 1b of the first section 1 of the vertically stacked structures 100 may employ various thickness T5 for the shell 30 of the metal oxide, e.g., $TiO_2$ coating, for discriminative light intensity sensing; and a core 25 of pure "naked" noble metal nanoparticles and/or their alloys for sensing light of various wavelengths. As noted above, the second layer 1b of the first section 1 may have a composition selected from three options. In a first option, the second layer 1b of the first section 1 of the vertically stacked structure 100 may be a mixture of noble metal alloy nanoparticles with shell core nanostructures (SCNs) of various sizes. In a second option, the second layer 1b of the first section 1 of the vertically stacked structure 100 may be composed of noble metal alloy nanoparticles, in which different functional units may have different alloys compositions that can correspond to the different wavelengths. In a third option, the second layer 1b of the first section 1 of the vertically stacked structure 100 may be composed of shell core nanostructures (SCNs) of various sizes.

Figure 5:
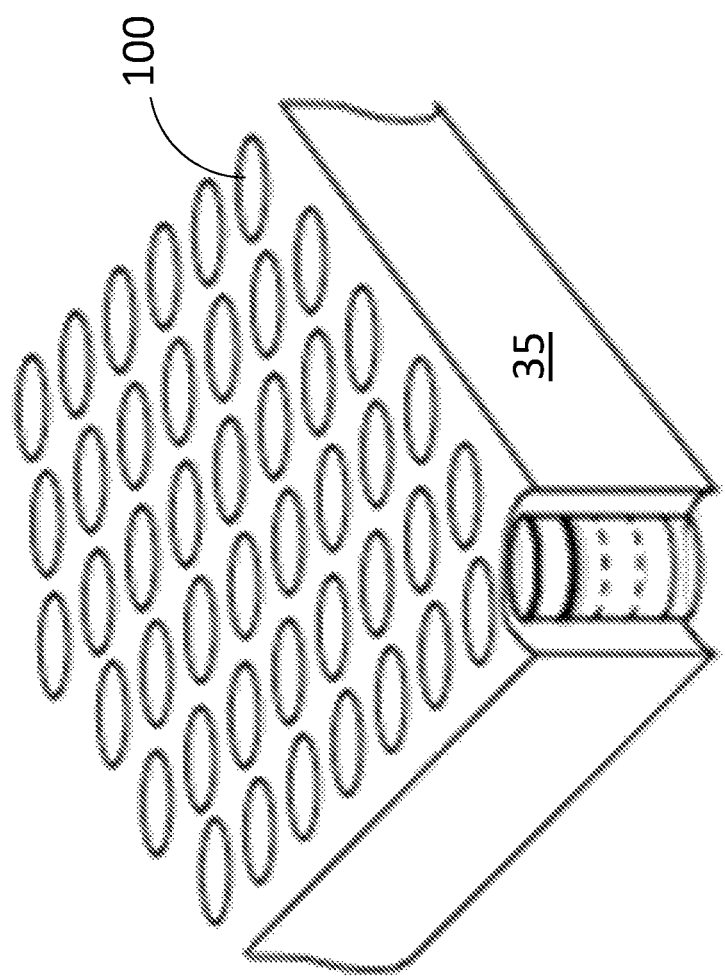
FIG. 5 is a perspective view of an array of the stacked unit depicted in FIG. 1, in which the stacked units provides a dispersed structure within a matrix of dielectric material.

The stacked structures 100 may be employed in a structure for receiving photons (light), as depicted in FIG. 5. In one embodiment, the stacked structures 100 may be integrated into a form factor for receiving photons that can include a bundle of insulated cable, in which the stacked structures 100 provide the core of each cable. In another embodiment, the stacked structures 100 may be integrated into a brush form factor for receiving photons. In yet another embodiment, the stacked structures 100 may be integrated into a polymeric plate 35, as depicted in FIG. 4. In one embodiment, the polymer plate 35 may be cross-linked polyethylene having a thickness ranging from 150 nm to 250 nm. In one example, the thickness of the polymeric plate 35 may be 200 nm. In some embodiments, the vertically stacked structures 100 may be present within openings formed in the polymeric plate 35 having a diameter substantially equal to the diameter of the vertically stacked structures 100. For example, the hole may be formed with laser drilled. In some examples, the diameter of the holes through the polymeric plate 35 may have a diameter on the order of approximately ~40 nm.

In each of the aforementioned form factors, the first section 1 of the vertically stacked structures 100 may be positioned to face a light source, i.e., positioned to receive photons.

In some embodiments, in the plurality of vertically stacked structures 100 that are employed for each of the aforementioned form factors, a core unit for the light intensity sensing vertically stacked structure 100 is centrally positioned in the plurality of stacked structure, in which the vertically stacked structure 100 that provides the core unit has a diameter of about 100 nm. In some examples, the vertically stacked structure 100 that provides the core unit may include shell core nanoparticles (SCNs) 100 with various thicknesses for the metal oxide shells 30, e.g., $TiO_2$ shells, of the shell core nanoparticles. In some embodiments, the vertically stacked structure 100 that provide the core unit include SnO-nanocluster modified anatase $TiO_2$ to enhance charge separation.

In some embodiments, in the plurality of vertically stacked structures 100 that are employed for each of the aforementioned form factors, peripheral units of vertically stacked structures 100 may be positioned around the vertically stacked structure 100 that provides the core unit. In some embodiments, the peripheral units may have a diameter of about 50 nm each. In some embodiments, the composition of the noble metal employed in the second layer 1p of the vertically stacked structure 100 may be varied to absorb different wavelengths. For example, the Au/Pt alloys can range from 90/10 percent ratio for the red part of the spectrum to 30/70 percent ratio for the violet part of the spectrum, respectively. Various ratios of shell 30 thicknesses and noble metal compositions can be employed in the core and peripheral units of the vertically stacked structures 100, keeping in mind that on average the ratio rods to cons ratio in humans is approximately 20:1.

Having described preferred embodiments of a photosensitive multilayered composite material suitable for eye implants (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A multilayered microstructure comprising:
a light receiving section including at least one layer including a noble metal composition and a metal oxide composition, the light receiving section transducing an energy of photons received to energies of electrons;
a piezo composite amplifier layer comprising a piezo polymer matrix, a first dispersed phase of piezo nanoparticles and a second dispersed phase of carbon nanotubes, the piezo composite amplifier amplifying a signal from the energies of the electrons received from the light receiving section using piezo-electric effects; and
an environmental interface layer for delivering the signal received from the piezo composite amplifier layer to a biological environment.

2. The multilayered micro structure of claim 1, wherein the at least one layer including the noble metal composition comprises core shell nanoparticles (CSN) comprising a core particle having a noble metal element and a shell having a metal oxide composition.

3. The multilayered microstructure of claim 2, wherein the noble metal element of the core particle is selected from the group consisting of gold (Au), iridium (Jr), platinum (Pt), silver (Ag) and combinations thereof.

4. The multilayered microstructure of claim 3, wherein the metal oxide of the shell is titanium oxide ($TiO_2$).

5. The multilayered microstructure of claim 4, wherein the light receiving section includes a first layer for the light receiving section comprising titanium dioxide or titanium dioxide with modification of anatase with SnO[Sn(II)], and a second layer for the light receiving section having a dielectric polymer matrix and dispersed phases of core shell nanoparticles (CSN) and carbon nanotubes.

6. The multilayered microstructure of claim 4, wherein the light receiving section includes a first layer for the light receiving section comprising titanium dioxide or titanium dioxide with modification of anatase with SnO[Sn(II)], and a second layer for the light receiving section being a solid noble metal layer.

7. The multilayered microstructure of claim 6, wherein the solid noble metal layer is treated with a plasma to provide pixilation.

8. The multilayered microstructure of claim 4, further comprising at least one layer of graphene at an interface of the light receiving section and the piezo composite amplifier layer.

9. The multilayered microstructure of claim 4, further comprising at least one two dimensional hybrid organic-inorganic perovskite film at an interface of the light receiving section and the piezo composite amplifier layer.

10. The multilayered microstructure of claim 1, wherein the piezo composite amplifier layer comprises three sublayers, wherein a first sublayer that is closest to the light receiving section comprises piezo polymer in an amount ranging from approximately 15 wt. % to approximately 20 wt. %, piezo nanoparticles in an amount ranging from approximately 75 wt. % to 80 wt. %, and carbon nanotubes (CNT) in an amount ranging from approximately 0.1 wt. % to approximately 0.5 wt. %.

11. The multilayered microstructure of claim 10, wherein a middle second sublayer of the three sublayers includes piezo polymer in an amount ranging from approximately 25 wt. % to 35 wt. %, piezo nanoparticles in an amount ranging from approximately 65 wt. % to 75 wt. %, and carbon nanotubes (CNTs) in an amount ranging from 0.2 wt. % to 0.6 wt. %.

12. The multilayered microstructure of claim 11, wherein a third sublayer of the three sublayers that is closest to the environmental interface layer comprises piezo polymer in an amount ranging from approximately 25 wt. % to 35 wt. %, piezo nanoparticles in an amount ranging from approximately 65 wt. % to 75 wt. %, and carbon nanotubes (CNTs) in an amount ranging from 0.2 wt. % to 0.6 wt. %.

13. The multilayered microstructure of claim 1, wherein the environmental interface layer is a biological environment interface layer comprising noble metal nanoparticles embedded in the dielectric polymer.

14. The multilayered microstructure of claim 1, wherein the environmental interface layer comprises a noble metal alloy grid.

15. The multilayered microstructure of claim 1, wherein the environmental interface layer comprises silver nanowires.

* * * * *